United States Patent [19]

Holmes et al.

[11] Patent Number: 5,017,562

[45] Date of Patent: May 21, 1991

[54] CRYSTALLINE SAPONIN-CONTAINING COMPLEX

[75] Inventors: Thomas J. Holmes, Saint Paul; Barbara G. Nygaard, Minneapolis, both of Minn.

[73] Assignee: Regents of the University of Minnesota, Minneapolis, Minn.

[21] Appl. No.: 418,896

[22] Filed: Oct. 5, 1989

Related U.S. Application Data

[63] Continuation of Ser. No. 13,464, Feb. 11, 1987, abandoned.

[51] Int. Cl.$^5$ ............................................... C07J 21/00
[52] U.S. Cl. ......................................... 514/26; 536/6; 540/18
[58] Field of Search ................. 540/18; 514/26; 536/6

[56] References Cited

U.S. PATENT DOCUMENTS

| | | | |
|---|---|---|---|
| 3,144,337 | 8/1964 | McKeen et al. | 99/2 |
| 3,169,959 | 2/1965 | Printy et al. | 260/55 |
| 3,883,425 | 5/1975 | Dorn | 424/195.1 |

FOREIGN PATENT DOCUMENTS

| | | | |
|---|---|---|---|
| 1140059 | 11/1962 | Fed. Rep. of Germany . | |
| 753137 | 7/1956 | United Kingdom | 540/18 |

OTHER PUBLICATIONS

Hale et al., Proc. Soc. Exp. Biol. Med., 1961, 161:486-489.
Wall et al., J. Biol. Chem., 1952, 198, 533-543.
*The Merck Index*, 9th ed., 1976, Merck & Co., Inc., Rahway, N.J., p. 1084.
Oakenfull, Food Chemistry, 1981, 6:19-40.
Woodbury et al., Economic Botany, 1961, 15:79-86.
Robinson, The Organic Constituents of Higher Plants, 1963, Burgess Publ. Co., Minneapolis, Minn., pp. 140-142, 159-164, and 170-172.
Sucrow et al., Phyto Chemistry, 1975, 14, 539-542.
Wilkomirski et al., Phytochemistry, 1975, 14, 2657-2659.
Marker et al., J. Am. Chem. Soc., 1947, 69, 2389-2392.
Oser, Fd. Cosmet. Toxicol., 1966, 4, 57-61.
Dewidar et al., Planta Medica, 1971, 19, 87-91.
Walter et al., J. Am. Chem. Soc., 1954, 76, 2271-2273.
Kobayashi, I., J. Chem. Soc. Perkin I, 1982, 2795.
Kitagawa, Chem. Pharm. Bull., 24, 121-124, (1976).
Kawano, Agric. Biol. Chem., 41(1), 1-8, (1977).
Kimura, J.C.S. Perkins I, 1923, (1981).

*Primary Examiner*—Mark Berch
*Attorney, Agent, or Firm*—Merchant, Gould, Smith, Edell, Welter & Schmidt

[57] ABSTRACT

A composition of matter is provided comprising a crystalline saponin-containing complex, wherein said crystalline complex is derived from a steroidal-saponin-containing plant material. Said crystalline complex is derived from a saponin-containing plant material by forming a mixture comprising saponin-containing aqueous plant extract solids and a mixture comprising methanol, acetone and water in a volume ratio of about 0.1-20:0-.1-20:1.0, and allowing the solution to stand at ambient temperature and pressure for a period of time sufficient to form the crystalline saponin-containing complex while plant fats and non-saponin carbohydrates remain substantially in solution.

14 Claims, 6 Drawing Sheets

FIG. 1A

SMILAGENIN

FIG. 1B

HECOGENIN

FIG. 1C

TIGOGENIN

CRYSTALLINE SAPONIN-CONTAINING COMPLEX

This is a continuation of application Ser. No. 07/013,464 filed Feb. 11, 1987 now abandoned.

BACKGROUND OF THE INVENTION

Steroidal sapogenins are known to be useful animal growth stimulators. For example, McKeen et al. (U.S. Pat. No. 3,144,337), the disclosure of which is incorporated herein by reference, disclose animal feeds containing selected steroidal sapogenins that elicit a substantially greater growth increase and feed efficiency response in animals, as compared to feeds which do not contain sapogenins. The beneficial effect of steroidal sapogenins as animal growth stimulants is further discussed by W.H. Hale et al., 1961, Proc. Soc. Exp Biol Med. 106, P. 486-489, the disclosure of which is incorporated herein by reference. McKeen et al. also report that when steroidal sapogenins are concurrently administered with estrogenic substances, such as diethylstilbestrol (DES), estradiol, and the like, the animals exhibit growth responses well beyond those which would be expected from the administration of estrogenic substances alone. However, because substances such as DES are suspected to be carcinogens, and are not always approved as animal growth stimulants, there is an increasing need for materials which will allow efficient incorporation of steroidal sapogenins into animal feeds.

Figure 1A:
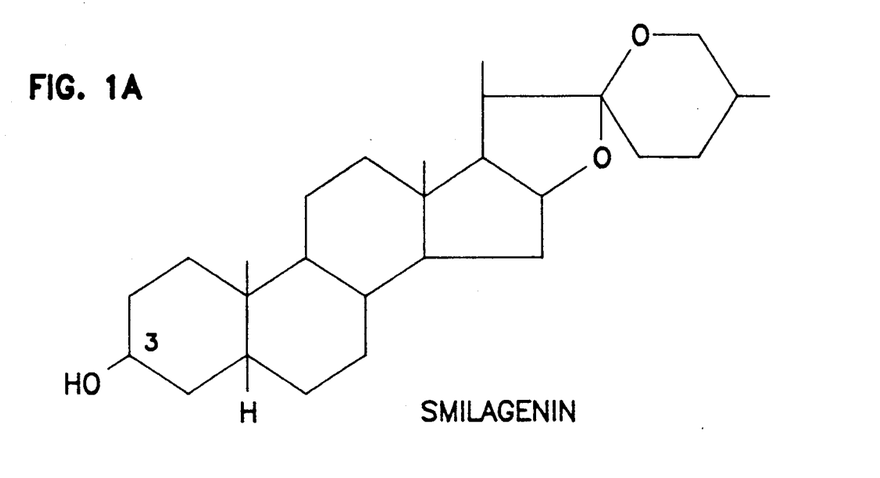
FIG. 1 is a schematic illustration of the molecular structure of three steroidal sapogenins, smilagenin, hecogenin and tigogenin. These sapogenins are the glycoside-hydrolyzed aglucone moieties of the corresponding steroidal saponins. Steroidal saponins would have glycosidic groups attached by means of an ether linkage at the C-3 carbon atom. The C-3 carbon atom is numbered in accord with standard steroidal nomenclature.
Figure 1B:
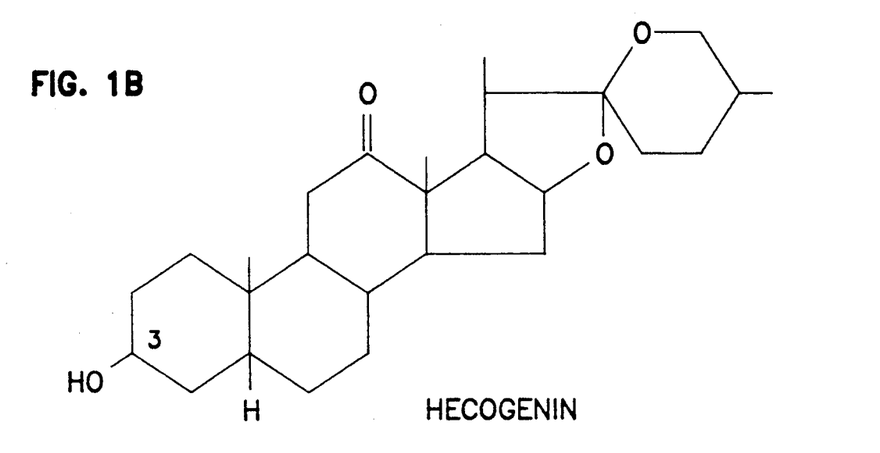
Figure 1C:
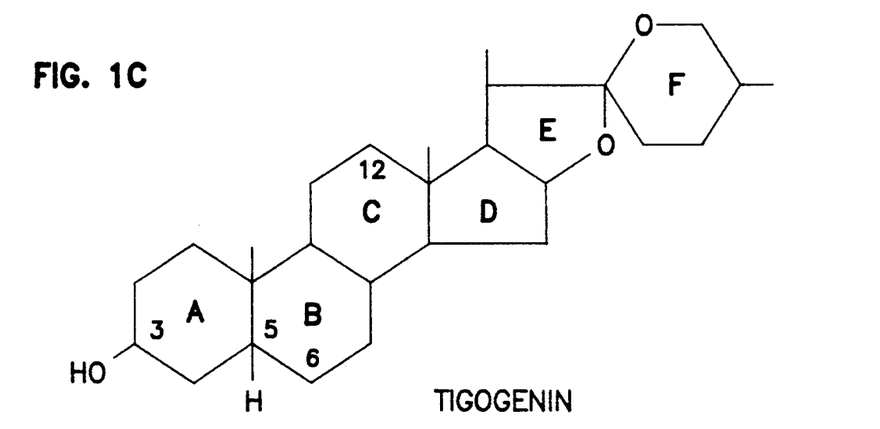

Sapogenins are the acid hydrolysis products of saponins, which are amphiphilic, steroidal or triterpenoid glycoside compounds. Crude extracts containing saponins can be obtained from a wide variety of plant materials. The steroidal saponins, and the steroidal sapogenins derived therefrom, possess the growth stimulating characteristics discussed hereinabove, are characterized by a glycosidic moiety, such as a 5- or 6-membered sugar moiety or a chain of sugar moieties, attached to a steroid moiety by means of an ether linkage at the carbon-3 (C-3) position. The structure of such a steroid moiety is exemplified by the structures of the sapogenins smilagenin, hecogenin and tigogenin which are schematically illustrated in FIG. 1. These structures are representations of sapogenins which would result from hydrolysis of the ether linkage between a glycoside moiety and a steroid moiety of a saponin molecule corresponding to each of these sapogenins. Saponins can be hydrolyzed in this way enzymatically or by exposure to acid.

Steroidal sapogenins are also useful as precursors for pharmaceutical steroids, such as cortisone and various hormones. See e.g. Wall et al., J. Biol. Chem. 198, 533-543; and Printy et al., U.S. Pat. No. 3,169,959.

For steroidal sapogenins to find wide use, an efficient, cost effective way of producing them must be made available. The difficulty of economically obtaining large quantities of steroidal sapogenins has apparently limited their use as animal growth stimulators, and as steroidal precursors.

Although crude aqueous plant extracts containing substantial amounts of steroidal saponins are easily obtained and are commercially available, it has been difficult to isolate the desired steroidal sapogenins from these sources. In addition to saponins, these crude extracts usually contain substantial amounts of plant fats and non-saponin carbohydrates. When these crude extracts are hydrolyzed with concentrated mineral acids, a virtually unusable, sticky, gumlike reaction product generally results. It is believed that the fats and free carbohydrates are responsible for forming this material. Once such a reaction product has formed, it is very difficult to efficiently extract the sapogenins therefrom.

Historically, saponins have been separated from fats and non-saponin carbohydrates by extracting crude aqueous plant extracts with butanol. This method is tedious, and can result in an oily gum which is difficult to handle in an efficient manner and which is not a suitable substrate for subsequent acid hydrolysis to produce sapogenins.

Another method of extracting saponins from plant material has been disclosed involving extraction with hot aqueous ethanol or isopropanol (85-95%). See Wall et al., 1952, J. Biol. Chem. 198, 533-543. The fats are subsequently extracted with benzene, and the saponins are then extracted from the aqueous alcohol solution with butanol. Following these steps, the saponins can be acid-hydrolyzed to form sapogenins. The crude product, however, still requires treatment with hot methanol potassium hydroxide to remove phenolic and acidic substances.

Although Printy et al. (U.S. Pat. No. 3,169,959) have disclosed a method for deriving smilagenin from a crude Agave extract without separating the saponin from the fats and non-saponin carbohydrates prior to hydrolysis, the yield was very low. Smilagenin is considered to be a particularly desireable sapogenin, both for use as a pharmaceutical precursor, and as an animal growth stimulator. Printy et al. extracted pulverized plant material with warm water. The extract was clarified and then hydrolyzed with mineral acid. The crude smilagenin precipitate was isolated and further extracted with heptane to give a 1% yield of smilagenin.

Given the usefulness of steroidal sapogenins as animal growth stimulants and steroid precursors, it will be appreciated that a need exists for a readily obtainable source of steroidal saponins which is substantially free of fats and non-saponin carbohydrates, and which is, therefore, easily hydrolyzed to form steroidal sapogenins. It will be further appreciated that a need exists for an efficient method of producing such an intermediate.

BRIEF DESCRIPTION OF THE INVENTION

The present invention provides a composition of matter comprising a crystalline saponin-containing complex, wherein the crystalline complex is derived from a steroidal saponin-containing plant material. The crystalline complex is preferably derived from saponin-containing plant material of a species selected from the group of plants consisting of *Agave, Yucca, Dioscorea, Quillaja, Medicago* and *Cyamopsis*, more preferably from a species of *Yucca*, even more preferably from a species of *Yucca* selected from the group consisting of *Yucca gloriosa, Yucca mohavensis, Yucca schidigera, Yucca brevifolia, Yucca augustifolia, Yucca glauca, Yucca elata, Yucca whipplei, Yucca bacatta, Yucca carnerosana, Yucca schottii* and *Yucca aloifolia*, most preferably from *Yucca schidigera*.

The crystalline saponin-containing complex of the present invention yields sapogenins in a yield of at least about 5% by weight when hydrolyzed with aqueous mineral acid. Hydrolysis of a preferred embodiment of the crystalline complex will yield a sapogenin, preferably smilagenin, in a yield of at least about 5% by weight. The crystalline complex of the present invention is substantially free of plant fats and non-saponin carbohydrates. Because of its relatively pure form, the present composition has utility as an intermediate in the production of sapogenins, preferably smilagenin, which are useful for a variety of purposes.

The present invention further provides a method of forming a crystalline saponin-containing complex comprising forming a mixture of about 1-20% by weight steroidal saponin-containing extract solids in a fluid comprising a fat solvent, methanol and water in a volume ratio of about 0.1-20:0.1-20:1.0, so that the saponins, fats and non-saponin carbohydrates are dissolved in said fluid. The mixture is allowed to stand at ambient temperature and pressure for a period containing complex while the fats and non-saponin carbohydrates remain substantially in solution. In a preferred embodiment, the fat solvent is acetone. Preferably, the present invention further provides the method above wherein evaporation of the fluid in step (b) is constrained such that evaporation of the fluid does not proceed at a rate or to an extent which causes the precipitation of the fats and non-saponin carbohydrates which are dissolved in the fluid. Preferably, evaporation of the fluid is constrained such that no more than 50% of the original fluid volume evaporates prior to isolation of the crystalline complex.

The present method further comprises isolating the crystalline saponin-containing complex and then hydrolyzing it to convert at least about 20% by weight of the saponins of the crystalline complex into sapogenins. In a preferred embodiment, the crystalline complex is hydrolyzed with an amount of aqueous mineral acid effective to convert at least about 50% by weight of the saponins of the crystalline complex into sapogenins.

The present invention further provides a crystalline saponin-containing composition derived from steroidal saponin-containing plant material which is prepared by a process comprising the following steps. A mixture is formed consisting essentially of one volume of an aqueous plant extract containing about 40% by weight of steroidal saponin-containing plant extract solids, and four volumes of a solvent consisting essentially of methanol, acetone and water in a volume ratio of about 1:1:1. The saponins, fats and non-saponin carbohydrates derived from the plant material are dissolved in the solution of methanol, acetone and water. Preferably, any insoluble material is separated by filtration means. The filtrate is placed in a container effective to constrain evaporation at ambient temperature and pressure such that evaporation of the filtrate does not proceed at a rate or to an extent which causes the precipitation of the fats and non-saponin carbohydrates which are in solution. The solution is then allowed to stand at ambient temperature and pressure for a period of time effective to form saponin-containing crystals while retaining the fats and non-saponin carbohydrates substantially in solution.

The present invention provides a crystalline intermediate which is useful for the production of sapogenins which are in turn useful as steroid precursors and as animal growth stimulants. In the past, the isolation of saponins has been difficult and time consuming. Given the relative difficulty of obtaining a saponin fraction which is a suitable intermediate for the hydrolytic production of sapogenins, the availability of a crystalline saponin-containing complex which can be obtained by a straightforward process will greatly improve the cost effectiveness of sapogenin production. It is believed that the present invention provides the first example of a crystalline saponin-containing complex which is substantially free of fats and non-saponin carbohydrates and, therefore, is a suitable intermediate for the hydrolytic production of sapogenins.

The crystalline complex isolated in Example V below has been shown by x-ray diffraction analysis to have regularly repeating interatomic bond lengths and bond angles which indicate that the complex does indeed have a crystalline structure. This is confirmed by data from studies of the crystalline complex using nuclear magnetic resonance (NMR) and infrared (IR) spectroscopy as discussed hereinbelow.

In the context of the present invention, the term "substantially free of fats and non-saponin carbohydrates" means that the crystals contain no significant amount of fats and non-saponin carbohydrates either as integral constituents or as impurities or contaminants. In the context of the present invention a fat solvent is defined as a fluid in which fats are highly soluble.

DETAILED DESCRIPTION OF THE INVENTION

Saponins and Sapogenins

Saponins are amphiphilic steroidal or triterpenoid glycoside compounds which are widely found constituents of a variety of different plant species. Saponins typically include glycosidic moieties which may comprise one or more sugar moieties such as pentose, hexose, or the like, which are linked to a steroid or triterpenoid group called a sapogenin. Saponins and sapogenins are described in *The Merck Index* (9th ed., Windholz et al., Editors, Merck & Co., Inc., Rahway, N.J., 1976) at page 1084, the disclosure of which is incorporated by reference herein.

There are two types of saponins: (a) glycosides of triterpenoid alcohols; and (b) glycosides of a particular steroid structure comprising a spiroketal side chain. Both types are soluble in water, methanol and ethanol but insoluble in ether. Aglucones of saponins, called sapogenins, are prepared by acid or enzymatic hydrolysis. Without attached sugar moieties, sapogenins have the solubility characteristics of other steroids and triterpenoids.

Steroidal sapogenins, which are the aglucone moieties of steroidal saponins, can be produced by hydrolyzing the bond between the glycosidic moiety and the steroidal sapogenin moiety of a steroidal saponin molecule. This bond is typically an ether linkage which is easily hydrolyzed by a number of methods which are well known in the art. As mentioned above, the hydrolysis may be catalyzed by enzymes or by acid. Acidcatalyzed hydrolysis is generally preferable. The most preferred method of hydrolysis is via aqueous mineral acids, such as hydrochloric acid (HCl), sulfuric acid ($H_2SO_4$), nitric acid ($HNO_3$), and the like.

Figure 2:
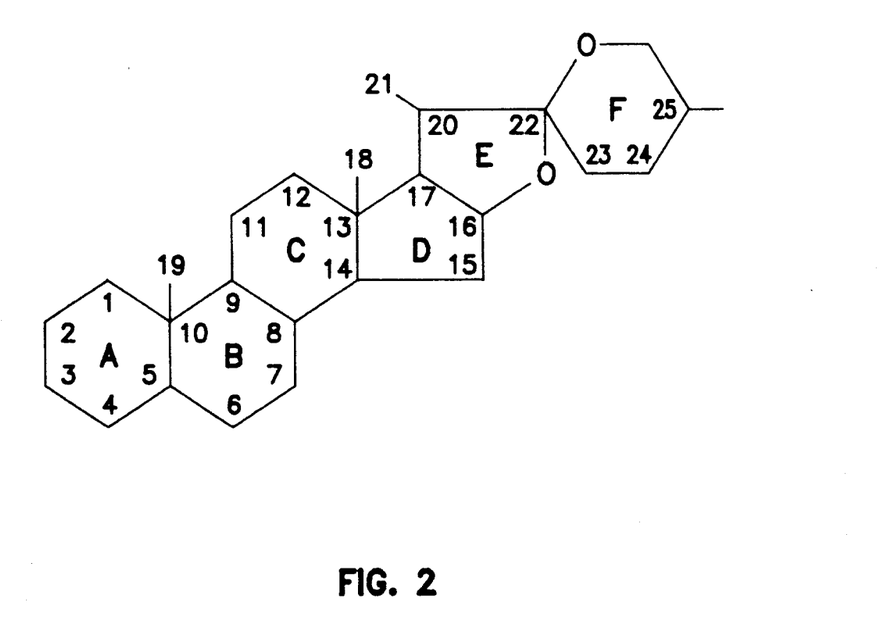
FIG. 2 is a schematic illustration of the steroidal nucleus of the class of sapogenins which are the glucose-hydrolyzed aglucone moieties of the corresponding steroidal saponins. Steroidal saponins would have saccharidic groups attached to the C-3 carbon atom. The rings are designated A-F, and the ring carbon atoms are numbered in accord with standard steroidal nomenclature.

The spiroketal steroid nucleus of the steroidal saponins is schematically illustrated in FIG. 2. Rings E and F contain the same basic carbon skeleton as the common animal steroids but lack the extra carbon atoms found in most plant sterols. Glycosylation is generally at C-3. [A variety of different monosaccharides such as glucose, galactose, xylose, and the like, can be present at C-3, as can oligosaccharides made up of a variety of different monosaccharides. Uronic acids can also be present.]

Many saponins found in plant extracts have been characterized. They include digitonin, dioscin, gitonin, filiferine (A+B), Agave saponin E, agavoside C, yuccoside, protoyuccoside, sarsasaponin, smilonin, kammonin, and the like. Some of these saponins are listed in Table I below along with respective results of research regarding their reported melting points and elemental analysis.

TABLE I

| | Melting Range (°C.) | Elemental Analysis (% C,H) |
|---|---|---|
| Filiferine A | 292 | Not Reported |
| Filiferine B | 319–308 | Not Reported |
| Agave saponin E | 304–308 | Not Reported |
| Agavoside C | 275 | Not Reported |
| Yuccoside | 276–278 | Not Reported |
| Protoyuccoside | 183–184 | Not Reported |
| Sarsasaponin | 241–245 | C, 59.8; H, 8.0 |
| Smilonin | 235–237 | C, 54.9; H, 7.7 |
| Kammonin | 310–315 | C, 52.2; H, 7.3 |

The glycosidic moieties of saponin molecules are generally soluble in polar solvents such as water, methanol, and the like, whereas the steroid moieties of steroidal saponins are generally more soluble in nonpolar solvents.

Although Applicants do not wish to be held to a theory of action with regard to how the crystalline saponin-containing complex is formed, Applicants believe that the methanol solvent portion of the methanol-water solution associates with the steroidal saponins in such a way in that the saponins are free to form hydrophobic bonds and to orient to one another in such a way that a repeating crystalline complex structure is formed. Applicants believe that when saponins are hydrated by water in an aqueous solvent, the water prevents the steroid moieties of the saponin molecules from interacting in such a way that hydrophobic bonds can be formed. When methanol replaces water as the solvent in direct association with the steroid moieties, and perhaps the saponin molecule generally, it is believed that this association frees the steroid moieties of the saponins to associate and to form hydrophobic bonds. These hydrophobic interactions act to orient the saponin molecules in such a way that a crystalline complex of saponin molecules is able to form.

Saponins are known to act as surfactants. Aqueous extracts of the Yucca plant contain significant quantities of saponins. This extract has been used as a non-photosensitive emulsifying agent by film manufacturers, and as a surfactant to increase the rate and amount of moisture addition to grain prior to dry rolling or steam flaking grain. Yucca extract is also used to form the stable foam or 'head' associated with draft root beer and can also be used as a flavor and/or coloring agent. Although sapogenins are believed to be of greater value than crude saponins, Yucca extract has been used to improve the feed efficiency of feed fed to cattle and sheep and has also been used to reduce odor caused by the excrement of swine and poultry raised in confined systems.

Steroidal sapogenins have been identified as precursors for the synthesis of cortisone and useful pharmaceutical hormones. Wall et al., 1952, Jour. Biol. Chem. 198, 533–543. McKeen et al. (U.S. Pat. No. 3,144,337), the disclosure of which is incorporated by reference herein, disclose the use of steroidal sapogenins to increase the weight of gain for domestic animals such as poultry, lambs, cattle, swine and the like, when fed feed containing certain selected steroidal sapogenins. Such feeds elicit a substantially greater growth increase and feed efficiency response in animals than when feeds without sapogenins are used. McKeen et al. report that there is a general improvement in the quality of the meat produced from the animals which are treated in this manner. They further disclose that the sapogenins employed are non-toxic in nature and preferably selected from a group consisting of smilagenin, sarsasapogenin and hecogenin.

Saponins can be found in a wide variety of plants. For example, they may be found in plant material used for human foods such as soybeans, kidney beans, mung beans, chick peas, asparagus, sugar beets, yams, peanuts, oats and spinach. A review of saponins found in foods has been published by D. Oakenfull (*Food Chemistry*, 1981, 6, 19–40) the disclosure of which is incorporated herein by reference. Steroidal saponins are most common in the plant families Liliaceae, Amaryllidaceae and Dioscoraceae. Plants containing steroidal saponins include species of Agave, Yucca, Dioscorea, Quillaja, Medicaqo, Cyamoosis. Preferred sources of steroidal saponins include *Agave americana, Agave variegata, Agave lecheguilla, Dioscorea floribunda, Cyamoosis tetragonolobus, Medicago sativa, Yucca gloriosa, Yucca mohavensis, Yucca schidigera, Yucca brevifolia, Yucca augustifolia, Yucca glauca, Yucca elata, Yucca whipplei, Yucca bacatta, Yucca carnerosana, Yucca schottii* and *Yucca aloifolia.*

The composition of the present invention can be derived from any steroidal-saponin-containing plant species. Preferred embodiments of the composition of the present invention are derived from Agave and Yucca species, preferably species of the Yucca plant, more preferably *Yucca schidigera, Yucca brevifolia, Yucca augustifolia, Yucca glauca, Yucca elata, Yucca whipplei, Yucca bacatta, Yucca aloifolia, Yucca mohavensis* or *Yucca gloriosa*, most preferably *Yucca schidigera*.

The composition of the present invention may be derived from cells or cell cultures having the genetic capability of providing the necessary cellular mechanisms to produce steroidal saponins. These cells or cell cultures may be of any derivation, microbial, plant, animal, or the like, so long as they are capable of producing steroidal saponins. It is intended that plants, plant materials and plant species, as they are defined herein, will include cells or cell cultures having genetic material derived from or fashioned after genetic material of plants.

Saponin-Containing Agueous Extract Solids

Saponin-containing aqueous plant extract solids are the materials remaining when liquid plant extracts are completely dried, as in Example II below. The saponin-containing aqueous extract solids used in the present invention may be a finely divided powder or they may be suspended in a fluid mixture.

Saponins can be extracted from plant materials in a variety of ways which are well known in the art. Saponins are soluble in many fluids including water, methanol, ethanol, butanol, isopropanol and the like. A simple water extraction of saponin-containing plant material will yield an aqueous saponin-containing extract. A crude saponin extract may also be produced using methanol to extract plant materials previously extracted with acetone or diethyl ether to remove lipids and pigments. Other methods which can be used include extraction with a 4:1 ethanol-water solvent, followed by subsequent defatting of the extract with benzene, and transfer of the saponins to a butanol phase to substantially free the saponins of proteins and sugars. Hot aqueous extractants can also be used.

Another method used primarily for isolating steroidal saponins involves extraction with hot aqueous ethanol or isopropanol (75 to 95% by weight alcohol). The aqueous alcohol extraction fluid is filtered and concentrated and the fat-soluble material is removed by mixing the extraction fluid with benzene. The saponins are subsequently extracted from the aqueous phase with butanol.

For the purpose of preparing the compositions of the present invention, and for use in the present method, a simple aqueous extract is preferred, but any method of extracting saponins from the bulk of the plant material can be used. In the preferred method, the plant material is pulverized or otherwise fragmented. A preferred source of saponin-containing extract is Yucca trees. The trees are cut up into logs and the logs, which contain considerable moisture, are converted into chips. The chips are then soaked in water and pressed to drive out aqueous saponin-containing fluids. The aqueous extracts are collected and concentrated, as by evaporating the water in an open air holding vat. A bacteriostat or bactericide, such as copper sulfate or sodium benzoate or the like, is generally used to limit bacterial growth in the extract while it is concentrated. Typically, the saponin-containing plant extract is concentrated until it has a solids content of about 20-60% solids by weight.

Saponin-containing aqueous Yucca extracts are commercially available from Extract Distributors Processing (EDP) Inc., Porterville, Calif. This product is available as a 40% solids extract of Yucca. Applicant believes that this product is derived from *Yucca schidigera*.

Fat Solvents

The term "fat solvent" as used herein is intended to include any liquid with which fat will associate when the liquid is mixed with water and methanol. This solvent is preferably miscible or at least partially miscible, in methanol and water. The fat solvent can be acetone, methyl vinyl ketone, methyl ethyl ketone, N-methyl pyrrolidine, tetrahydrofuran or the like. Preferably, the fat solvent is acetone. In the context of this invention, two liquids which are "miscible" can mix to the extent that both are found in a single liquid phase. A partially miscible liquid mixes so that at least 1% by volume of the liquid can be found in a liquid phase containing a larger percentage of the other liquid or liquids.

Formation of the Crystalline Saponin-Containing Complex

The crystalline saponin-containing complex is formed by forming a mixture of about 1-20% by weight, preferably 5-15% by weight of steroidal-saponin-containing extract solids in a fluid comprising a fat solvent, methanol and water in a volume ratio of about 0.1-20:0.1-20:1.0, so that the saponins, fats and non-saponin carbohydrates are dissolved in the fluid. The mixture is then allowed to stand at ambient temperature and pressure for a period of time effective to form the crystalline saponin-containing complex, while the fats and non-saponin carbohydrates remain substantially in solution. In a preferred embodiment, the fat solvent is acetone. Preferably, insoluble residue in the mixture is removed prior to allowing the crystals to form. In a more preferred embodiment the mixture comprises methanol, acetone and water in a volume ratio of about 0.2-10:0.2-10:1.0, more preferably about 0.25-5:0.25-5:1.0, and most preferably about 0.5-2.0:0.5-2.0:1.0.

In a preferred embodiment, the crystalline saponin-containing complex is formed by forming a mixture consisting essentially of about one volume of an aqueous steroidal-saponin-containing plant extract containing about 5-75% by weight plant solids, preferably 20-60% by weight plant solids, with about four volumes of a solvent consisting essentially of methanol, acetone and water in a volume ratio of 0.5-2.0:0.5-2.0:1.0, such that the saponins, fats and non-saponin carbohydrates derived from the plant extract are dissolved in the liquid phase of the mixture. The liquid phase is then allowed to stand at ambient temperature and pressure for a period of time effective to form the crystalline saponin-containing complex, while the fats and non-saponin carbohydrates remain substantially in solution. In a preferred embodiment, insoluble residue in the mixture is removed prior to allowing the crystals to form.

After the insoluble residue has been optionally removed, the solution is preferably placed in a container which limits air flow to the surface of the fluid, and/or to the air space immediately above the fluid surface, such that evaporation of the fluid is constrained. This may be accomplished by placing the solution in a flask such as an Erlenmeyer flask, a round-bottom flask, or any suitable container which in some way constricts air flow to the surface of any fluid contained therein or to the air space immediately above the fluid. It is possible to put the solution in a container which may be sealed for part or all of the time in which the solution is contained therein. The object is to constrain evaporation of the fluid such that evaporation does not proceed at a rate or to an extent which causes the precipitation of the fats and nonsaponin carbohydrates which are dissolved in the fluid. Many of the most suitable containers for this purpose are described in the Corning Glassworks Catalogue (*The Lab Book;* Corning Glassworks, Inc.; 1983, Corning, N.Y.) which is incorporated herein by reference. The containers include round-bottom flasks, Erlenmeyer flasks, volumetric flasks, reagent bottles, and the like.

The solution is allowed to stand in the container at ambient temperature and pressure for a period of time sufficient to form the crystalline saponin-containing complex. However, any temperature and pressure which will allow the formation of the saponin-containing complex crystals may be used. The crystals are typically formed at atmospheric pressure and at room temperature which may be from about 10-37° C., preferably about 20-30° C., although higher and lower temperatures are not known to prevent crystallization. The period of time necessary to obtain crystals may be anywhere from about 1 to 200 days, preferably about 5 to 100 days, most preferably about 15-60 days.

In preferred embodiments, the evaporation is constrained to limit the evaporation of the original solution to no less than about half of its original volume. If evaporation is allowed to proceed too far beyond about 50% of the original solution volume, the product can be contaminated with unwanted amounts of non-saponin carbohydrates and fats. Preferably, the rate of evaporation is limited to about 1.0% a day, more preferably, about 0.1%.

In the most preferred embodiment, the crystalline saponin-containing complex is prepared by a process comprising the following steps:

(a) forming a mixture consisting essentially of one volume of aqueous plant extract containing about 20-60% by weight of steroidal-saponin-containing plant extract solids, and four volumes of a solvent consisting essentially of methanol, acetone and water in a volume ratio of about 1:1:1, so that the saponins, fats and non-saponin carbohydrates derived from said plant material are dissolved in solution;

(b) separating any insoluble material from the mixture by filtration to yield a filtrate;

(c) placing the filtrate in a container effective to constrain evaporation at ambient temperature and pressure such that evaporation of the filtrate does not proceed at a rate or to an extent which cause the precipitation of the fats and nonsaponin carbohydrates which are in solution; and (d) allowing the filtrate to stand at ambient temperature and pressure for a period of time effective to form saponin-containing complex crystals, while substantially retaining the fats and non-saponin carbohydrates in solution.

The formation and/or nucleation of the crystalline saponin-containing complex can be aided in any suitable manner, such as by "seeding" the solution with previously isolated complex crystals, by placing a rough surface in the solution to aid nucleation, by mild agitation during the period when the solution is allowed to stand, or the like.

When the crystals have formed, they may be collected in any suitable manner. The solution may be poured or decanted off and then washed in cold water and collected by centrifugation, vacuum filtration, or the like. The crystals may be dissolved and recrystallized from similar solvent mixtures as recommended for the initial crystallization or from any other suitable solvent, such as methanol, alcohol, butanol, methanol and water, or the like.

The saponin-containing crystals are typically white, although they may from time to time be slightly off-white, or even have a slightly brown tint which makes them a light tan color. When the crystals are heated, they discolor in a range from about 270-280° C., typical from about 272-278° C., most typically from about 274-276° C. When further heated the crystals melt in a melting range of about 285-305° C., more preferably about 290-300° C. The melting range is the range between the temperature at which the crystals begin to melt and the temperature at which all of the crystals are melted as further defined in Example V below.

Almost all pure elements and compounds are capable of forming crystals because they are substantially homogeneous and, therefore, interact in a repetitive manner on the molecular level. A perfect crystal is one in which the crystal structure would be that of an ideal space lattice. No such crystals are believed to exist. All real crystals have imperfections which influenced the physical properties of the crystals. The purer the crystal, the more regular the interactions and the more consistent the melting range and other physical properties. Evidence that would indicate that a solid is indeed a crystal, includes evidence that the solid has a narrow melting range. Other evidence generally includes the availability of clear spectrographic data for infrared (IR) spectroscopy, nuclear magnetic resonance (NMR) spectroscopy, and x-ray diffraction analysis. In each case, data which show relatively sharp and distinct peaks, are generally considered to indicate that the sample is a relatively pure substance. In the case of x-ray diffraction patterns, clear and distinct peaks are generally considered to indicate that a crystalline structure does exist, and that there are repeating structural interactions which would only be seen if this sample was in fact crystalline in nature. Such data has been collected for the present crystals and is included in the Figures and Examples herein below.

In addition, elemental analysis of the crystals indicates that the crystals contain about 54-58% by weight carbon (C), about 6-10% by weight elemental hydrogen (H), and about 34-38% by weight elemental oxygen (O). In a preferred embodiment, the crystals contain about 55-57% by weight C. The analysis was done by complete combustion analysis, methods for which are well known in the art.

Samples of the complex crystals were also analyzed for impurities by thin-layer chromatography. The results indicated that the crystals are substantially free of fats and non-saponin carbohydrates derived from the plant. This means that the crystals contain very little if any fats and/or non-saponin carbohydrates, preferably less than about 3% by weight, more preferably less than about 1% by weight, and even more preferably less than about 0.1% by weight.

In the thin-layer chromatography method used in Example XII, a sample containing the crystals isolated in Example V gave a chromatogram which showed the samples to be substantially free of plant fats and non-saponin carbohydrates. Studies of impure saponin-containing extracts show a solid streak from rf 0 through 1.0. The sample containing crystals from Example V, however, showed several large spots corresponding to saponins which appeared between rf 0.3 and rf 0.7.

Above rf 0.7 where the fats are characteristically located, and below rf 0.3 where the non-saponin carbohydrates are characteristically located, there were substantially no spots. Although some faint spots did develop above rf 0.7 and below rf 0.3 indicating some impurities, the crystals were substantially free of fats and non-saponin carbohydrates.

Figure 3:
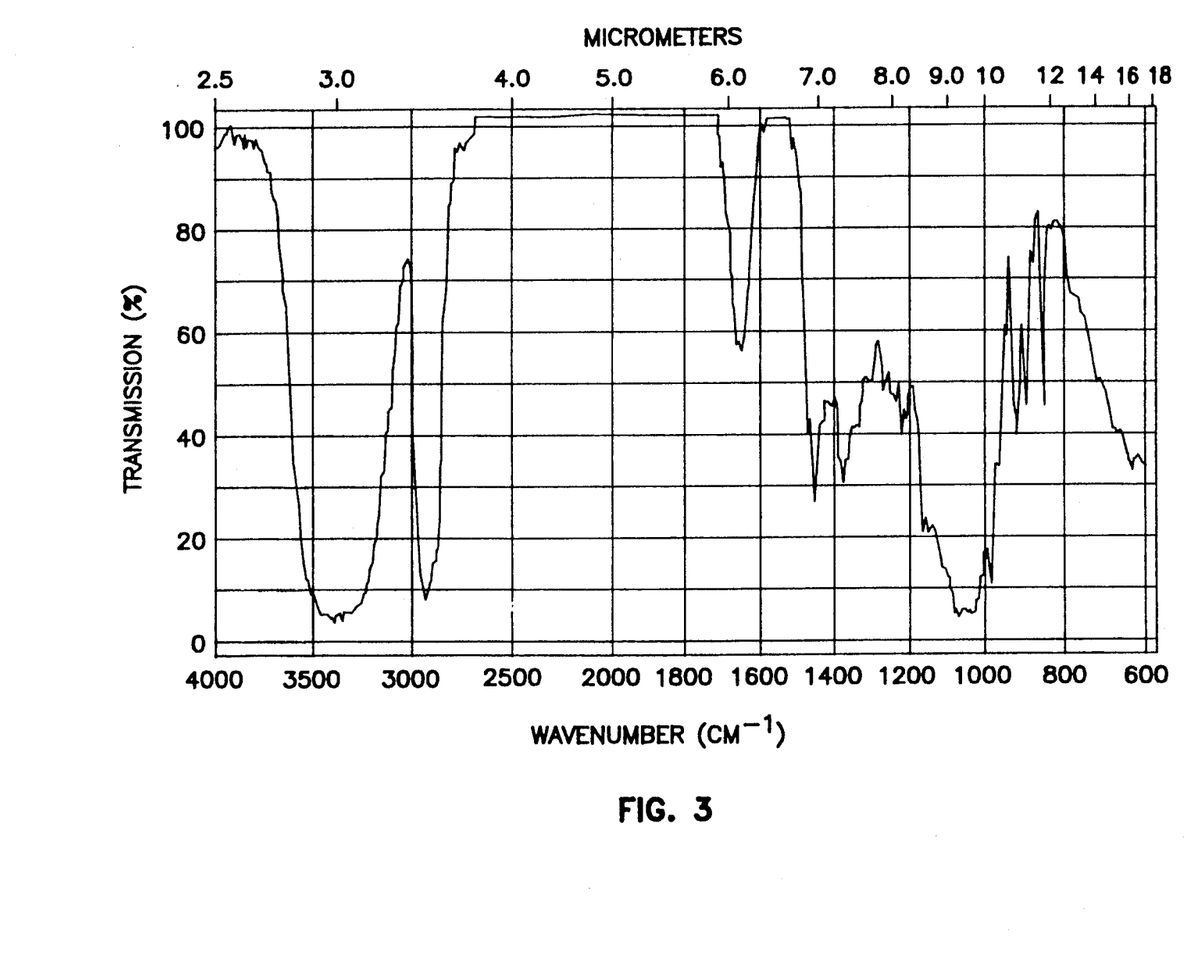
FIG. 3 is a reproduction of an infrared (IR) spectrum obtained for a sample of the crystalline saponin-containing complex of the present invention isolated in Example V below.
Figure 4:
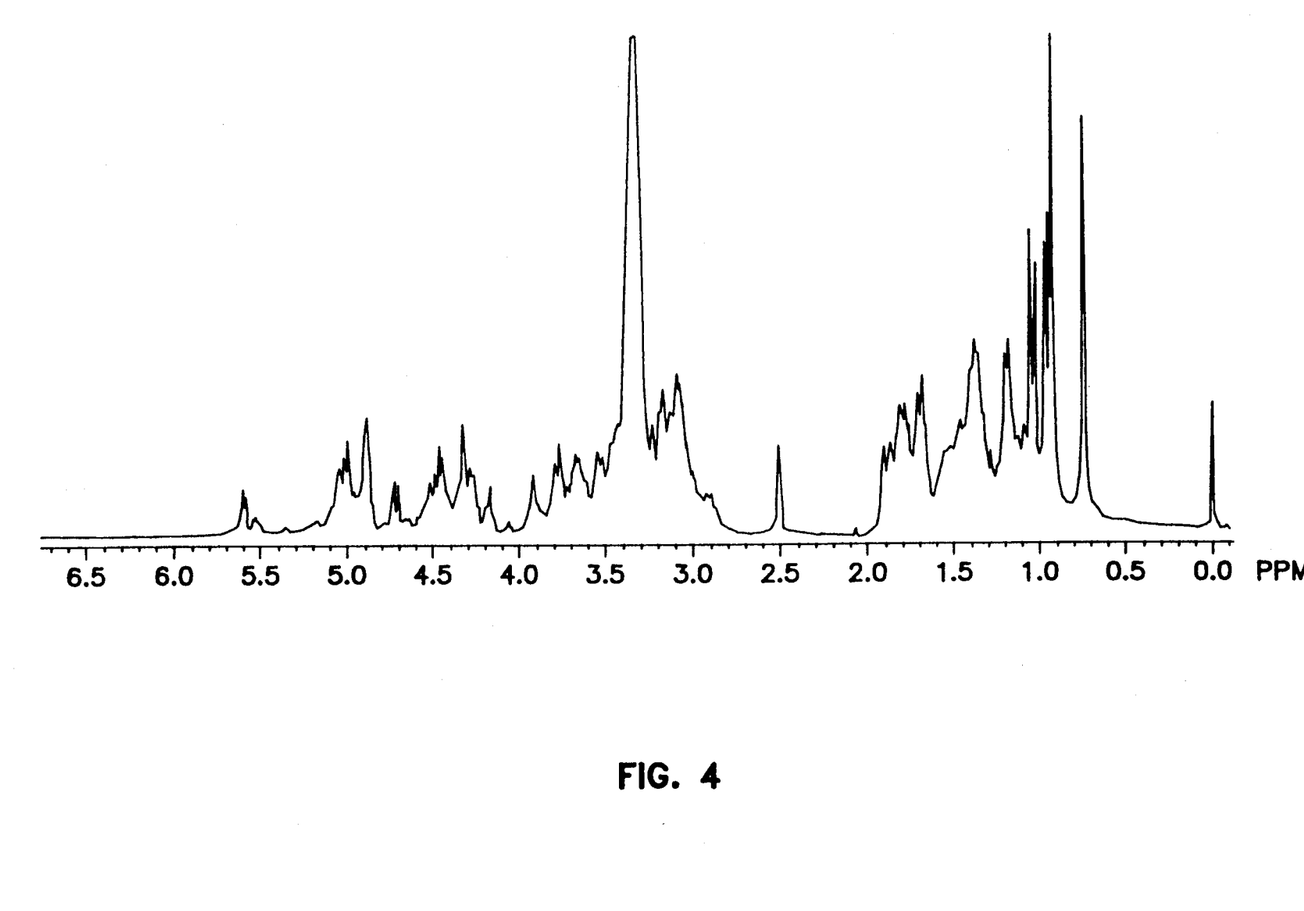
FIG. 4 is a reproduction of a $^1$H-nuclear magnetic resonance (NMR) spectrum of a sample of the crystalline saponin-containing complex of the present invention isolated in Example V below.
Figure 5:
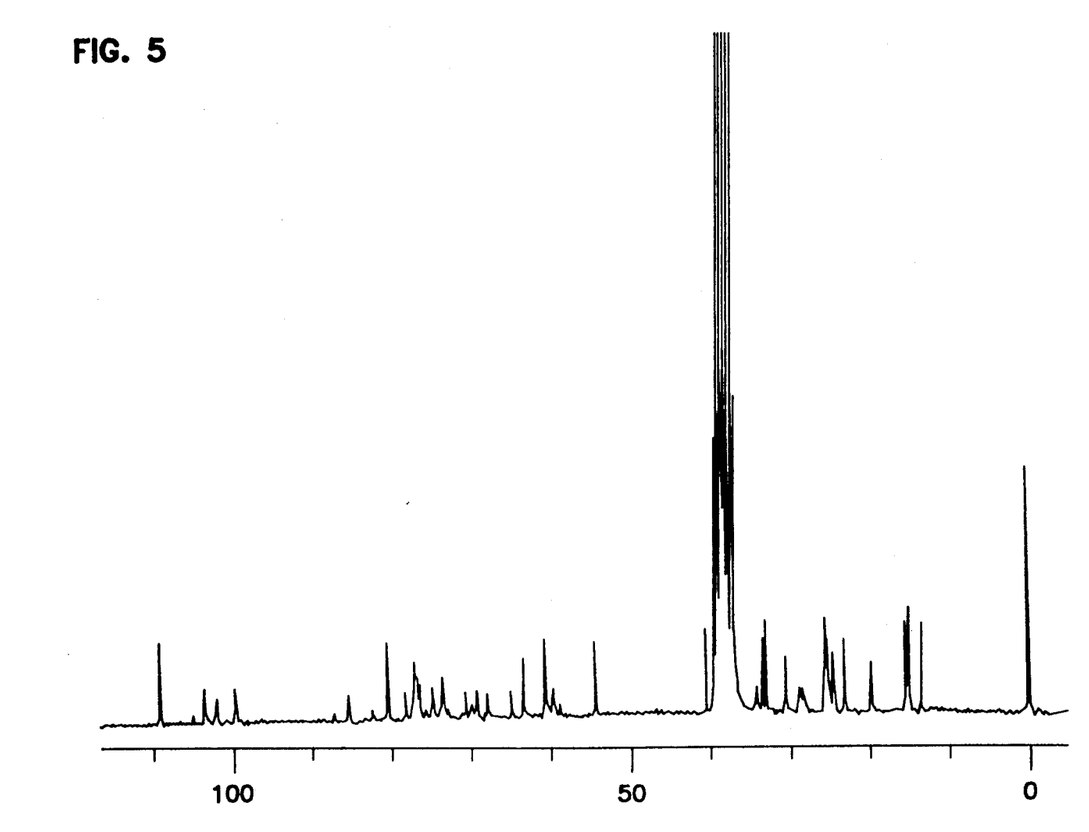
FIG. 5 is a $^{13}$C-nuclear magnetic resonance (NMR) spectrum of a sample of the crystalline saponin-containing complex of the present invention isolated in Example V below.
Figure 6:
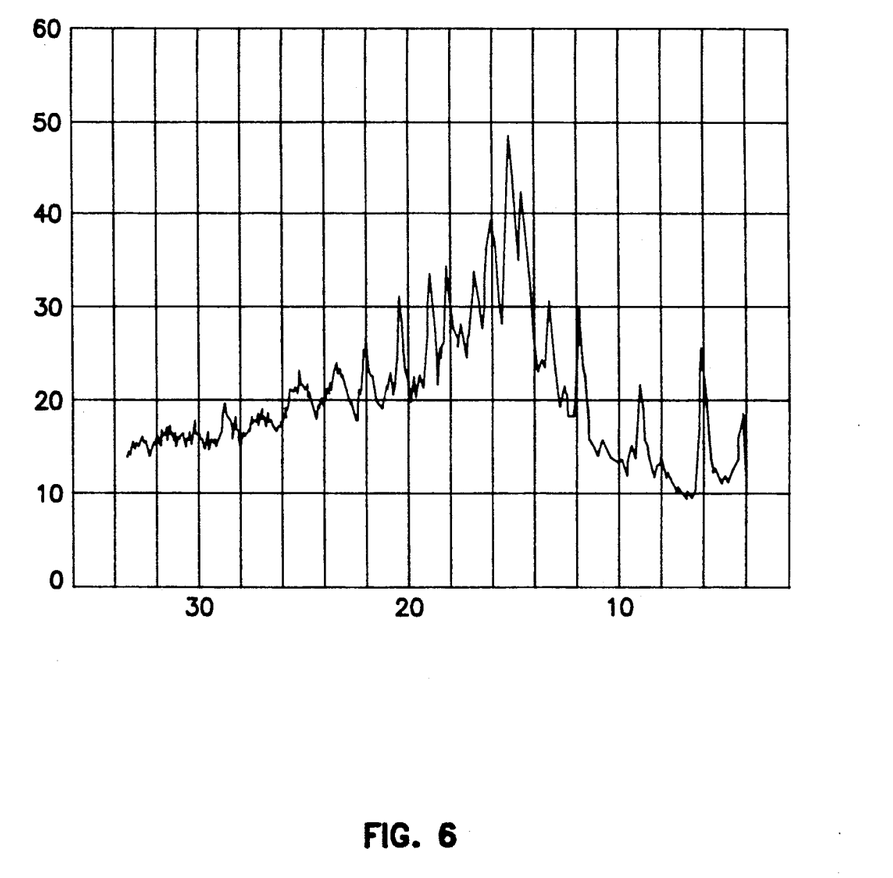
FIG. 6 is a reproduction of an x-ray diffraction pattern of a sample of the crystalline saponin-containing complex of the present invention isolated in Example V below.

Further indications of the crystals' purity were manifest in the sharp x-ray diffraction pattern shown in FIG. 6, as well as the precise spectral data obtained by infrared (IR) (FIG. 3) and NMR analysis (FIGS. 4 and 5). In each case, the well defined peaks are indicative of a consistent composition which allows sharply defined data measurements.

Hydrolysis Procedure

The saponin-containing complex crystals can be hydrolyzed to form sapogenins by a process catalyzed by acid or by enzymes. The sapogenins are formed from the saponins incorporated in the complex crystals by hydrolyzing the ether linkage between the sapogenin moiety and the glycosidic moiety of each saponin molecule. This process can be catalyzed by an enzyme which will hydrolyze such an ether linkage, but is preferably catalyzed with acid, most preferably with an aqueous mineral acid, such as hydrochloric acid (HCl), sulfuric acid ($H_2SO_4$), nitric acid ($HNO_03$), or the like. The aqueous mineral acid may be from about 0.1 N to a concentrated aqueous solution of the acid. In the most preferred embodiment, 4 N HCl is used.

Hydrolysis of the crystalline saponin-containing complex of the present invention yields a product which contains about 1-70%, preferably about 5-40%, more preferably about 10-30% by weight of sapogenins. In the preferred embodiment, the yield of a sapogenin, preferably smilagenin, is about 1-50% by weight, preferably about 5-35% by weight, more preferably about 10-25% by weight. This yield is determined by gravimetric analysis (weighing the product) and by thin-layer chromatographic comparison to known samples of smilagenin. In the most preferred embodiment, hydrolysis of the crystalline saponin-containing complex from *Yucca schidigera* gives a yield of about 14-18% smilagenin. Of the saponins of the crystalline complex, acid hydrolysis is effective to convert at least about 20%, preferably about 50%, more preferably about 75% into sapogenins.

The invention will be further described by reference to the following detailed examples.

EXAMPLE I

Aqueous Saponin-Containing Yucca Extract

The plant material of a *Yucca schidigera* tree is cut up and pulverized. The pulverized plant material is soaked in water for 24 hours and then pressed to drive out the aqueous saponin-containing Yucca extracts. The aqueous extracts are collected and concentrated by evaporation in an open-air holding vat. A bacteriostat, sodium benzoate is added in an amount effective to make a 0.01 molar solution of sodium benzoate in order to limit bacterial growth in the extract fluid. The saponin-containing liquid extract is concentrated until it has a solids content of about 40% by weight.

EXAMPLE II

Saponin-Containing Yucca Extract Solids

The saponin-containing liquid extract of Example I is further evaporated under ambient conditions until a dry powder remains.

EXAMPLE III

Methanol, Water, Crystallization

One volume of the aqueous saponin-containing extract of Example I containing about 50% by weight solids is added to 4 volumes of a mixture of reagent grade methanol and water in a volume ratio of 1:1. The suspension is efficiently mixed by manually shaking the mixture in an Erlenmeyer flask. The solution is then allowed to stand approximately 10-20 minutes and the insoluble residue is removed by vacuum filtration through filter paper (Whatman Qualitative #1 —medium fast; Whatman, Inc.; Clifton, N.J.) in a Buchner funnel. A clear brown solution resulted. This solution is allowed to stand for 3 weeks at ambient temperature and pressure in a 2000 ml Erlenmeyer flask (number 4980-2L; Corning Glassworks, Inc.; Corning, N.Y.). The saponin-containing complex crystals form as a white solid crystalline mass on the walls of the container. After standing for 3 weeks the solution is poured off and the crystalline complex is collected from the walls of the flask by loosening the crystals with a stainless steel spatula. The crystals are washed into a Buchner funnel and are collected and separated from the fluid by filtration means using Whatman #1 filter paper. Evaporation during the 3 weeks is slowed by the constricted neck of the flask such that the solution volume at the end of that time is 80% of the original solution volume.

EXAMPLE IV

Methanol, Acetone and Water Solution

One volume of an aqueous saponin-containing Yucca extract containing about 40% by weight solids (Yucca Extract; EDP, Inc.; Porterville, Calif.) was added to 4 volumes of a mixture of reagent grade methanol and acetone and water in a volume ratio of 1:1:1. This mixture was mixed manually by shaking the mixture in a liter round-bottom flask (number 4280-1L; Corning Glassworks, Inc.; Corning, N.Y.). The solution was allowed to stand approximately 10 minutes. The insoluble residue was then removed by vacuum filtration of the fluid through filter paper (Whatman Qualitative #1 —medium fast; Whatman, Inc.; Clifton, N.J.) in a Buchner funnel. A clear brown solution resulted. This solution was allowed to stand in a liter round-bottom flask (number 4280-1L; Corning Glassworks Inc.; Corning, N.Y.) at ambient temperature and pressure in a laboratory room for 3 weeks. Formation of the complex crystals was aided by "seeding" the solution with previously isolated crystalline saponin-containing complex derived from *Yucca schidigera* extracts. The saponin-containing complex crystals formed as a white solid crystalline mass on the walls of the container. Evaporation of the solution was such that the solution volume at the end of this period of time was 75% of the original solution volume. The solution was poured off after the 3 week period ended. The crystals were loosened with a stainless steel spatula and removed by filtration through filter paper (Whatman #1) in a 30 Buchner funnel.

EXAMPLE V

Methanol, Acetone, Water Crystallization

To 110 ml of a saponin-containing Yucca extract containing about 40% by weight solids (Yucca Extract; EDP, Inc.; Porterville, CA) was added a mixture of equal volumes (150 ml each) of water and reagent grade methanol and acetone. This suspension was mixed manually by shaking until almost all of the solids were in solution. The mixture was then allowed to stand for approximately 15 minutes. Insoluble residue was then removed by vacuum filtration through filter paper (Whatman Qualitative #1 —medium fast; Whatman, Inc.; Clifton, N.J.) in a Buchner funnel. The resulting solution was allowed to stand at room temperature (approximately 23° C.) for 5 weeks in an unsealed 1000 ml round-bottom flask (number 4280-1L; Corning Glassworks, Inc., Corning, N.Y.). The round-bottom flask showed the evaporation to a rate of about 1-3 ml per day. The saponin complex formed as a white solid crystalline mass on the walls of the container. Evaporation was not allowed to exceed one-half the original volume. The crystalline saponin-containing complex was isolated from the residual liquid by vacuum filtration through filter paper (Whatman Qualitative #1—medium fast) in a Buchner funnel. The white crystalline complex was found to be substantially free of contaminating lipid and carbohydrate plant materials.

EXAMPLE VI

Melting Range

The crystalline saponin-containing complex isolated in Example IV above was heated in a Thomas-Hoover Capillary Melting Point Apparatus (Arthur H. Thomas, Co.; Philadelphia, Pa.) to determine the melting range. Crystals (1-2mg) were placed in an unsealed capillary tube and placing in the capillary melting apparatus. The temperature was allowed to increase at the rate of about 30 1-2° C. per minute through the melting range. The melting range is the range between the temperature at which liquid begins to form and the temperature at which no solid remained in the sample. The melting range for the crystals isolated in Example V above was 290°-300° C.

EXAMPLE VII

Elemental Analysis

The elemental analysis for the crystalline saponin-containing complex was done by M-H-W Laboratories, Phoenix, Ariz. by complete combustion analyses of samples provided from the complex crystals isolated in Example V above. The results were reported as a mean of four separate determinations. The values did not vary by more than ±0.5% among these samples. The crystals were reported to contain 56.3% by weight C, 8.0% by weight H, and 35.7% by weight O.

EXAMPLE VIII

Infrared (IR) Analysis of Yucca Saponin Complex

Approximately 2-3 mg of the crystals isolated in Example V were ground to a fine powder in a mortar. Potassium bromide (KBr) was added to this in a ratio of approximately 80 mg of KBr to 1 mg of crystals. The mixture was ground into fine powder, dried under a heat lamp for approximately 1 minute, transferred to a KBr pellet die and placed in a Carver Laboratory Press (Model #21000-261) under vacuum for 1.5 minutes. Subsequently, the pressure on the press was brought up to 20,000 pounds and allowed to remain there for 2.0 minutes. The pressure was then released slowly and the compressor which created the vacuum was turned off. The die was removed from the press and the transparent KBr pellet was removed. The pellet was then scanned using a Perkin-Elmer 281 Infrared Spectrophotometer under normal conditions: N slit; Abscissa Expansion setting =1; Ordinate Expansion setting =1; Mode Setting =%T; Suppression =ON; Time Drive =Off; and Scan Time =12 minutes.

The spectrum obtain is reproduced in FIG. 3. The peaks were ascribed to the following wavelengths [KBr pellet (cm$^{-1}$)]:3400 broad, 2940, 1640, 1453 sharp, 1380, 1260, 1060 broad, 922, 897, 852, 630 end.

EXAMPLE IX

$^1$H-Nuclear Magnetic Resonance (NMR) Spectrum

Approximately 20 mg of the crystals isolated in Example V above were dissolved in 0.5 ml of deuterated methyl sulfoxide (Dimethyl-d$_6$ sulfoxide (d$_6$-DMSO); Aldrich Chemical Company, Milwaukee, Wis.) and filtered through compressed glass wool into a 5mm×7 inch NMR tube. One drop of tetramethylsilane (TMS) was added as a reference standard. The sample was then scanned on a Nicolet-300 NMR (frequency 300 MHz) (Nicolet Instrument Co.; Madison, Wis.). The spectrum is reproduced in FIG. 4 below. Peaks at the following wavelengths were analyzed as follows: 0.00, reference standard (TMS); 0.71, steroid methyl singlet; 0.91-1.95, complex overlapping steroid resonances; 2.85-5.65, complex overlapping carbohydrate resonances plus oxygenated steroid resonances.

EXAMPLE X

$^{13}$C-Nuclear Magnetic Resonance (NMR) Spectrum

Approximately 60 mg of the crystals isolated in Example V above were dissolved in 4 ml of deuterated methyl sulfoxide (d$_6$-DMSO) and filtered through glass wool into a 10mm×7 inch NMR tube. One drop of tetramethylsilane (TMS) was added as a reference standard. The sample was then scanned on a Brucker WM-250 NMR (frequency 62.9 MHz) (USA Bruker Instruments, Inc; Billerica, Mass.). The spectrum is reproduced in FIG. 5 below. The spectrum exhibits sample associated peaks at the wavelengths listed below. The intensity of those peaks relative to TMS=100 is given in parenthesis: 14.36 (38), 15.85 (45), 16.10 (40), 20.36 (22), 23.40 (29), 25.33 (24), 25.47 (23), 26.08 (30), 26.23 (22), 26.37 (39), 29.44 (10), 29.83 (10), 31.33 (23), 34.45 (38), 34.82 (31), 35.55 (10), 38.05-40.49 (off-scale solvent signals), 41.49 (33), 55.63 (30), 60.70 (11), 61.48 (11), 61.80 (33), 64.19 (23), 65.78 (10), 68.09 (10), 69.36 (11), 70.62 (10), 73.24 (17), 73.46 (16), 74.58 (13), 76.07 (14), 76.40 (19), 76 48 (15), 76.65 (24), 77.77 (11), 80.31 (31), 85.01 (10), 99.60 (14), 101.84 (10), 103.39 (14), 108.74 (31). The peaks above 50 are considered to be peaks for carbohydrate moieties, and the peaks below 50, with exception of the very large series of peaks associated with the d$_6$-DMSO solvent which are clustered together at about 38 to 41, are considered to be associated with steroid moieties.

EXAMPLE XI

X-Ray Diffraction Pattern

An x-ray diffraction pattern was obtained using a Rigaku Model #2011 diffractometer (Rigaku Denki Co., Ltd; Tokyo, Japan). Approximately 250 mg of gently-powdered crystalline saponin-containing complex, isolated in Example IV above, was lightly compressed into a glass-slide well (1.6 cm×0.1 cm) and exposed to Ni-filtered CuKα radiation (25 kV×14 mA) at a scanning rate of 1° $2\theta\text{min}^{-1}$ for a forty-minute period during which time the diffraction pattern was recorded. The pattern is reproduced in FIG. 6. Analysis indicates that there were sharp peaks at the following $2\theta$ values (relative intensity): 6° (38), 9° (30), 12° (51), 13.5° (52), 14.5° (82), 15.4° (100), 16° (74), 17° (61), 18.4° (62), 19° (60), 20.5° (54), 22° (42).

EXAMPLE XII

Thin-Layer Chromatography (TLC) of Yucca Saponin Crystalline Complex

Approximately 80 μg of the crystalline saponin-containing complex isolated in Example V above dissolved in 30% methanol/chloroform was applied to the baseline of a HLF silica gel chromatographic plate (silica gel HLF (0.025×5×20 cm; Analtech Inc.; Newark, Del.). The plate was developed twice in an ascending manner with air-drying in between to provide better resolution. The eluent contained ethyl acetate, methanol, and water (EtOAc:MeOH:H$_2$O) in a volume ratio of 100:13.5:10. After a second air-drying, a 50% sulfuric acid aqueous solution was sprayed on the plates. After spraying, the plate was heated on a hot plate set at 100° C. for approximately 10 min. when the saponins were completely charred. A permanent record was obtained by photocopying the charred plate. Major components were observed at Rf: 0.34, 0.41, 0.47, 0.51, and 0.57 after two ascending elutions. The crude saponin-containing starting material used in Example V above was chromatographed on the sample TLC plate. No individual components could be distinguished from the solid streak remaining from rf 0 to 1.0.

EXAMPLE XIII

Acid Hydrolysis of the Saponin-Containing Crystalline Complex

A solution containing 1.0 gram of the saponin-containing crystalline complex isolated in Example V above, dissolved in 100 ml of methanol, was treated with concentrated hydrochloric acid to make the solution 4N in acid. The solution was then heated in a water bath at 85° C. Hydrolysis was complete after 1 hour when a white crystalline precipitate formed. Water (200 ml) was added and efficiently mixed by manually shaking the liquid mixture in a round-bottom flask until a solution was formed. The solution was extracted with 200 ml of chloroform in a separatory funnel. The chloroform phase was separated and evaporated to dryness. The residue was dissolved in 20% ethyl acetate/hexane, and decolorized by filtration through a layer of silica gel (230-400 mesh). The resulting clear filtrate was evaporated to provide smilagenin in a yield of 14-17% as determined by comparative thin-layer chromatography as described in Example XIV below.

EXAMPLE XIV

Acid Hydrolysis of the Crystalline Saponin-Containing Complex

A sample (50 mg) of the crystalline saponin-containing complex isolated in Example IV is placed in 200 ml round-bottom flask with 10 ml of methanol and 5 ml of concentrated hydrochloric acid (HCl). The mixture is swirled in the flask to dissolve the crystals and then heated in a water bath at 80° C. After heating for 1 hr, the solution is washed into a 200 ml separatory funnel with 30 ml of deionized water. The solution is mixed and 20 ml of chloroform is added. This mixture is shaken manually and then allowed to stand until the water and chloroform phases have separated. Ten (10) ml of saturated potassium hydroxide (KOH) are added to neutralize the HCl. The mixture is shaken again and then allowed to stand until the water and chloroform phases have separated. The chloroform phase is drawn off and evaporated to a dry residue in 200 ml round-bottom flask using a rotary evaporator.

A sample (0.5 mg) of the dry residue is dissolved in 1 ml of methanol. A sample of this solution (50 μl) is applied to a HLF silica gel plate (0.025 ×5×20cm; Analtech Inc.; Newark, Del.) along with known samples of smilagenin. The yield of smilagenin in the dry residue of 14-17% was determined by comparison of these samples after elution with an 80% hexane: acetone eluent and fixing with 50% aqueous H$_2$SO$_4$ as in Example XII above.

The invention has been described with reference to very specific preferred embodiments and techniques. However, it should be understood that many variations and modifications may be made while remaining with the spirit and scope of the present invention.

What is claimed is:

1. A composition comprising a crystalline saponin-containing complex of a multiplicity of saponin compounds, each having various glycoside attachments, which upon acid hydrolysis yields at least two sapogenins, and which is derived from a steroidal-saponin-containing plant species selected from the group consisting of *Yucca gloriosa, Yucca mohavensis, Yucca schidigera, Yucca brevifolia, Yucca bacatta, Yucca carnerosana, Yucca schottii, Yucca whipplei, Yucca bacatta, Yucca carnerosana, Yucca schottii, Yucca aloifolia, Agave americana, Agave variegata, Agave lecheguilla, Dioscorea floribunda, Cyamopsis tetragonolobus, Medicago sativa;* contains less than 3 percent by weight plant fats and non-saponin carbohydrates; discolors when heated to a temperature of about 270° to about 280° C.; and melts at a temperature of about 285° to about 305° C.;

which composition is prepared by a process comprising the steps of:

(a) forming a mixture consisting essentially of one volume of an aqueous plant extract containing about 40% by weight of said plant species extract solids, and four volumes of a solvent consisting essentially of methanol, acetone and water in a volume ratio of about 1:1:1, so that the saponins, fats and non-saponin carbohydrates derived from said plant solids are dissolved in solution;

(b) separating any insoluble material from the mixture by filtration to yield a filtrate;

(c) placing the filtrate in a container which constrains evaporation at ambient temperature and pressure in a manner such that evaporation of the filtrate does not proceed at a rate or to an extent which cause the precipitation of the fats and non-saponin carbohydrates which are in solution; and (d) allowing said filtrate to stand at ambient temperature and pressure for a period of time effective to form saponin-containing complex crystals, while substantially retaining the fats and non-saponin carbohydrates in solution.

2. The composition of claim 1 wherein one of the sapogenins derived from acid hydrolysis of the saponin-containing complex is smilagenin.

3. A composition of matter comprising a crystalline saponin-containing complex of a multiplicity of gylcosylated saponin compound which upon acid hydrolysis yield at least two sapogenins, wherein said crystalline complex is derived from a steroidal-saponin-containing plant species selected from the group consisting of *Yucca gloriosa, Yucca mohavensis, Yucca schidigera, Yucca brevifolia, Yucca augustifolia, Yucca glauca, Yucca elata, Yucca whipplei, Yucca bacatta, Yucca carnerosana, Yucca schottii, Yucca aloifolia, Agave americana, Agave variegata, Agave lecheguilla, Dioscorea floribunda, Cyamopsis tetragonolobus, Medicago sativa;* contains less than 3 percent by weight plant fats and non-saponin carbohydrates; discolors when heated to a temperature of about 270° to about 280° C.; and melts at a temperature of about 285° to about 305° C.

4. The composition of matter of claim 3 wherein one of the sapogenins derived from acid hydrolysis of the saponin-containing complex is smilagenin.

5. A composition according to claim 3 wherein the complex produces several spots between rf values 0.3 and 0.7 on a thin layer chromatograph taken on silica gel with 30 percent methanol in chloroform.

6. A composition according to claim 1 wherein the complex produces several spots between rf values 0.3 and 0.7 on a thin layer chromatograph taken on silica gel with 30 percent methanol in chloroform.

7. The composition of claim 3 having an elemental composition consisting essentially of about 54–58% by weight of carbon, about 6–10% by weight of hydrogen and about 34–38% by weight of oxygen; and which is white or off-white and has a melting point of about 290–300° C.

8. The composition of claim 3 wherein the crystalline saponin-containing complex exhibits an infrared (IR) spectrum as shown in FIG. 3.

9. The composition of claim 3 wherein the crystalline saponin-containing complex exhibits a nuclear magnetic resonance (NMR) spectra as shown in FIGS. 4 and 5.

10. The composition of claim 3 wherein the crystalline saponin-containing complex exhibits an x-ray diffraction pattern as shown in FIG. 6.

11. The composition of claim 1 having an elemental composition consisting essentially of about 54–58% by weight of carbon, about 6–10% by weight of hydrogen and about 34–38% by weight of oxygen, and which is white or off-white and has a melting point of about 290–300° C.

12. The composition of claim 1 wherein the crystalline saponin-containing complex exhibits an infrared (IR) spectrum as shown in FIG. 2.

13. The composition of claim 1 wherein the crystalline saponin-containing complex exhibits a nuclear magnetic resonance (NMR) spectra as shown in FIGS. 3 and 4.

14. The composition of claim 1 wherein the crystalline saponin-containing complex exhibits an x-ray diffraction pattern as shown in FIG. 5.

* * * * *

UNITED STATES PATENT AND TRADEMARK OFFICE
CERTIFICATE OF CORRECTION

PATENT NO. : 5,017,562  Page 1 of 2
DATED : 05/21/91
INVENTOR(S) : Holmes et al.

It is certified that error appears in the above-identified patent and that said Letters Patent is hereby corrected as shown below:

In column 3, line 13, after "period" insert --of time effective to form the crystalline saponin--.

In column 5, line 28, before the word "A" delete --[--.

In column 5, line 32, after the word "present" delete --]--.

In column 6, line 56, for "Medicaqo" read --Medicago--.

In column 6, line 56, for "Cyamoosis" read --Cyamopsis--.

In column 6, line 58, for "lecheguilla" read --lechequilla--.

In column 6, line 58, for "Cyamoosis" read --Cyamopsis--.

In column 11, line 4, for "ne" read --no--.

In column 11, line 29, for "($HNO_{03}$)," read --($HNO_3$),--.

In column 11, line 30, for "N" read --$\underline{N}$--.

In column 11, line 32, for "4 N HCl" read --4$\underline{N}$ HCl--.

In column 14, line 61, for "76 48" read --76.48--.

In column 15, line 38, after "plate." insert --A reproduction of the charred plate is shown in Figure 7.--.

In column 15, line 54, for "4N" read --4$\underline{N}$--.

In column 16, line 45, after "brevifolia," insert --Yucca augustifolia, Yucca glauca, Yucca elata, Yucca whipplei,--.

UNITED STATES PATENT AND TRADEMARK OFFICE
CERTIFICATE OF CORRECTION

PATENT NO. : 5,017,562

DATED : 05/21/91

INVENTOR(S) : Holmes et al.

It is certified that error appears in the above-identified patent and that said Letters Patent is hereby corrected as shown below:

In column 16, line 46, after the word "schohii" delete--Yucca whipplei, Yucca bacatla, Yucca carnerosana, Yucca schottii;--.

In column 16, line 48, for "lecheguilla" read --lechequilla--.

In column 17, line 15, for "compound" read --compounds--.

In column 17, line 23, for "lecheguilla" read --lechequilla--.

Signed and Sealed this

Ninth Day of February, 1993

Attest:

STEPHEN G. KUNIN

*Attesting Officer*     Acting Commissioner of Patents and Trademarks